(12) United States Patent
Mattei et al.

(10) Patent No.: US 7,205,309 B2
(45) Date of Patent: Apr. 17, 2007

(54) QUINAZOLINE DERIVATIVES

(75) Inventors: Patrizio Mattei, Riehen (CH); Werner Mueller, Aesch (CH); Werner Neidhart, Hagenthal le Bas (FR); Matthias Heinrich Nettekoven, Grenzach-Wyhlen (DE); Philippe Pflieger, Schwoben (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 256 days.

(21) Appl. No.: 10/613,782

(22) Filed: Jul. 3, 2003

(65) Prior Publication Data

US 2004/0029901 A1 Feb. 12, 2004

(30) Foreign Application Priority Data

Jul. 5, 2002 (EP) .................................. 02014904

(51) Int. Cl.
| | |
|---|---|
| A61K 31/55 | (2006.01) |
| A61K 31/54 | (2006.01) |
| A61K 31/517 | (2006.01) |
| C07D 239/72 | (2006.01) |
| C07D 413/00 | (2006.01) |
| C07D 417/00 | (2006.01) |
| C07D 419/00 | (2006.01) |

(52) U.S. Cl. .............. 514/266.3; 514/217.06; 514/217.07; 514/226.8; 514/228.2; 514/266.31; 514/266.2; 540/524; 544/55; 544/62; 544/96; 544/116; 544/284; 544/285; 544/287

(58) Field of Classification Search .............. 514/266.2, 514/266.21, 266.22, 266.23, 266.1, 266.3, 514/266.31, 217.06, 217.07, 226.8, 228.2; 544/283, 284, 291, 293, 285, 287, 55, 62, 544/96, 116; 540/524

See application file for complete search history.

(56) References Cited

U.S. PATENT DOCUMENTS

| | | | |
|---|---|---|---|
| 3,511,836 A * | 5/1970 | Hess ........................ 544/291 |
| 3,753,981 A | 8/1973 | Breuer et al. |
| 4,035,367 A | 7/1977 | Simpson .................... 544/363 |
| 4,598,089 A | 7/1986 | Hadvary et al. ............. 514/449 |
| 4,931,463 A | 6/1990 | Barbier et al. .............. 514/422 |
| 4,983,746 A | 1/1991 | Barbier et al. .............. 549/328 |
| 5,064,833 A * | 11/1991 | Ife et al. ................... 514/266.4 |
| 5,399,720 A | 3/1995 | Karpf et al. ................ 549/292 |
| 5,444,062 A * | 8/1995 | Coe et al. .............. 514/266.21 |
| 6,004,996 A | 12/1999 | Shah et al. ................. 514/449 |
| 6,573,263 B2 | 6/2003 | Niewohner et al. ......... 514/243 |

FOREIGN PATENT DOCUMENTS

| | | |
|---|---|---|
| EP | 0 185 359 | 6/1986 |
| EP | 0 189 577 | 8/1986 |
| EP | 0 443 449 | 8/1991 |
| EP | 0 524 495 | 1/1993 |
| EP | 0 669 324 | 8/1995 |
| FR | 2 100 916 | 3/1972 |
| WO | WO 92 07844 | 5/1992 |
| WO | WO 96 37474 | 11/1996 |
| WO | WO 99 09986 | 3/1999 |
| WO | WO 99/34786 | 7/1999 |
| WO | WO 00/09122 | 2/2000 |
| WO | WO 00/09123 | 2/2000 |
| WO | WO 01 23389 | 4/2001 |
| WO | WO 02 20488 | 3/2002 |
| WO | WO 02 094789 | 11/2002 |

* cited by examiner

Primary Examiner—James O. Wilson
Assistant Examiner—Tamthom N. Truong
(74) Attorney, Agent, or Firm—George W. Johnston; Dennis P. Tramaloni; Samuel H. Megerditchian

(57) ABSTRACT

Compounds of formula I

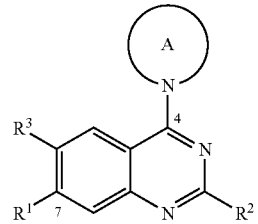

as well as pharmaceutically acceptable salts and esters thereof, wherein $R^1$, $R^2$, $R^3$ and A have the significance given in the specification are provided. The compounds can be used for the treatment or prevention of obesity.

16 Claims, No Drawings

QUINAZOLINE DERIVATIVES

BACKGROUND OF THE INVENTION

Neuropeptide Y is a 36 amino acid peptide that is widely distributed in the central and peripheral nervous systems. This peptide mediates a number of physiological effects through its various receptor subtypes. Studies in animals have shown that neuropeptide Y is a powerful stimulus of food intake, and it has been demonstrated that activation of neuropeptide Y Y5 receptors results in hyperphagia and decreased thermogenesis.

Therefore compounds that antagonise neuropeptide Y at the Y5 receptor subtype represent an approach to the treatment of eating disorders such as obesity and hyperphagia.

The current approach is aiming at medical intervention to induce weight loss or prevention of weight gain. This is achieved by interfering with appetite control, which is mediated by the Hypothalamus, an important brain region proven to control food intake. Herein, neuropeptide Y (NPY) has been proven to be one of the strongest central mediators of food intake in several animal species. Increased NPY levels result in profound food intake. Various receptors of neuropeptide Y (NPY) have been described to play a role in appetite control and weight gain. Interference with these receptors is likely to reduce appetite and consequently weight gain. Reduction and long-term maintenance of body weight can also have beneficial consequences on co-associated risk factors such as arthritis, cardiovascular diseases, diabetes and renal failure.

Accordingly, the compounds of formula I can be used in the prophylaxis or treatment of arthritis, cardiovascular diseases, diabetes, renal failure and particularly eating disorders and obesity.

SUMMARY OF THE INVENTION

The invention provides compounds of formula I and pharmaceutically acceptable salts and esters thereof, wherein
$R^1$ is —O—$R^4$ or —N($R^5$)($R^6$);
$R^2$ is alkyl or amino;
$R^3$ is hydrogen, alkyl or halogen;
$R^4$ is hydrogen, alkyl, alkoxyalkyl, hydroxyalkyl, aralkyl, substituted aralkyl, heterocyclylalkyl, substituted heterocyclylalkyl, cycloalkylalkyl, $NH_2$—$SO_2$—, amino-$SO_2$— or alkyl-$SO_2$—;
$R^5$ and $R^6$ are independently selected from hydrogen, alkyl, cycloalkyl, cycloalkylalkyl, alkylcarbonyl, cycloalkylcarbonyl, aryl, substituted aryl, aralkyl, substituted aralkyl, arylcarbonyl, substituted arylcarbonyl, alkoxyalkyl, hydroxyalkyl, heterocyclyl, substituted heterocyclyl, heterocyclylalkyl, substituted heterocyclylalkyl, heterocyclylcarbonyl, substituted heterocyclylcarbonyl, alkyl-$SO_2$—, aryl-$SO_2$—, substituted aryl-$SO_2$—, heterocyclyl-$SO_2$—, substituted heterocyclyl-$SO_2$, or amino-$SO_2$—, or
$R^5$ and $R^6$ together with the N atom to which they are attached form a 5- to 10-membered heterocyclic ring which optionally comprises a second heteroatom selected from nitrogen or oxygen and, wherein the substituted heterocyclyl ring has one or more substituents independently selected from alkyl and alkoxy; and
A is a 5 to 7-membered saturated unsubstituted or substituted heterocyclic ring comprising the nitrogen atom which is attached to the quinazoline ring and optionally a second heteroatom which is selected from oxygen, sulfur or nitrogen and, wherein the ring A substituted heterocyclic ring has one or more substituents independently selected from halogen, alkyl, alkoxy, haloalkoxy, cycloalkylalkoxy, hydroxy, amino, acetylamino, cyano, hydroxyalkyl, alkoxyalkyl, haloalkoxyalkyl and cycloalkylalkoxyalkyl.

The compounds of formula I and their pharmaceutically acceptable salts are neuropeptide ligands, for example neuropeptide receptor antagonists and in particular, they are selective neuropeptides Y Y5 receptor antagonists.

DETAILED DESCRIPTION OF THE INVENTION

The present invention is concerned with novel quinazoline derivatives useful as neuropeptide Y (NPY) receptor ligands, particularly neuropeptide Y (NPY) antagonists.

The invention provides compounds of formula I and pharmaceutically acceptable salts and esters thereof, wherein
$R^1$ is —O—$R^4$ or —N($R^5$)($R^6$);
$R^2$ is alkyl or amino;
$R^3$ is hydrogen, alkyl or halogen;
$R^4$ is hydrogen, alkyl, alkoxyalkyl, hydroxyalkyl, aralkyl, substituted aralkyl, heterocyclylalkyl, substituted heterocyclylalkyl, cycloalkylalkyl, $NH_2$—$SO_2$—, amino-$SO_2$— or alkyl-$SO_2$—;
$R^5$ and $R^6$ are independently selected from hydrogen, alkyl, cycloalkyl, cycloalkylalkyl, alkylcarbonyl, cycloalkylcarbonyl, aryl, substituted aryl, aralkyl, substituted aralkyl, arylcarbonyl, substituted arylcarbonyl, alkoxyalkyl, hydroxyalkyl, heterocyclyl, substituted heterocyclyl, heterocyclylalkyl, substituted heterocyclyl, heterocyclylcarbonyl, substituted heterocyclyl, carbonyl, alkyl-$SO_2$—, aryl-$SO_2$—, substituted aryl-$SO_2$—, heterocyclyl-$SO_2$—, substituted heterocyclyl-$SO_2$, or amino-$SO_2$—, or
$R^5$ and $R^6$ together with the N atom to which they are attached form a 5- to 10-membered heterocyclic ring which optionally comprises a second heteroatom selected from nitrogen or oxygen and, wherein the substituted heterocyclyl ring has one or more substituents independently selected from alkyl and alkoxy; and A is a 5 to 7-membered saturated unsubstituted or substituted heterocyclic ring comprising the nitrogen atom which is attached to the quinazoline ring and optionally a second heteroatom which is selected from oxygen, sulfur or nitrogen and, wherein the ring A substituted heterocyclic ring has one or more substituents independently selected from halogen, alkyl, alkoxy, haloalkoxy, cycloalkylalkoxy, hydroxy, amino, acetylamino, cyano, hydroxyalkyl, alkoxyalkyl, haloalkoxyalkyl and cycloalkylalkoxyalkyl.

The compounds of formula I and their pharmaceutically acceptable salts are neuropeptide ligands, for example neuropeptide receptor antagonists and in particular, they are selective neuropeptides Y Y5 receptor antagonists.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, 2-hydroxyethoxy, 2-methoxyethoxypreferably methoxy and ethoxy and most preferred methoxy.

The term "aryloxy" or substituted aryloxy, alone or in combination, signifies a group of the formula aryl-O— in which the term "aryl" or substituted aryl has the previously given significance, such as phenyloxy.

The term "aryl", alone or in combination, signifies a phenyl or naphthyl group, preferably a phenyl group. Substituted aryl is aryl which carries one or more substituents each independently selected from halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, and nitro. Typical aryl and substituted aryl include phenyl, chlorophenyl, trifluoromethylphenyl, chlorofluorophenyl, aminophenyl, methylcarbonylphenyl, methoxyphenyl, methylendioxyphenyl, 1-naphthyl and 2-naphthyl. Preferred is phenyl, 3-chlorophenyl, 3-trifluoromethylphenyl, 3-aminophenyl, 4-methylcarbonylphenyl, 4-methoxyphenyl and particularly phenyl.

The term "aralkyl" or substituted aralkyl, alone or in combination, signifies an alkyl or cycloalkyl group as previously defined in which one hydrogen atom has been replaced by an aryl group or substituted aryl, respectively, as previously defined. Preferred are benzyl, benzyl substituted with hydroxy, alkoxy or halogen, preferably fluorine. Particularly preferred is benzyl.

The term "heterocyclyl", alone or in combination, signifies a saturated, partially unsaturated or aromatic 4- to 10-membered heterocycle which contains one or more, preferably one ore two hetero atoms selected from nitrogen, oxygen and sulfur, wherein oxygen and particularly nitrogen are preferred. Substituted heterocyclyl is heterocyclyl substituted on one or more carbon atoms by halogen, alkyl, alkoxy, oxo, cyano, haloalkyl preferably trifluoromethyl and unsubstituted heterocyclyl, preferably morpholinyl and pyrrolidinyl, and/or on a secondary nitrogen atom (i.e. —NH—) by alkyl, cycloalkyl, aralkoxycarbonyl, alkanoyl, phenyl or phenylalkyl, or on a tertiary nitrogen atom (i.e.=N—) by oxido, with halogen, alkyl, cycloalkyl and alkoxy being preferred. The term "heterocyclyl" also includes the term heteroaryl. Examples of heterocyclyl groups are pyridinyl, pyrrolidinyl, piperidinyl, morpholinyl, piperazinyl, 3,4-dihydro-1H-isoquinolinyl, azepanyl, tetrahydrofuranyl and thiophenyl. Such heterocyclyl groups which are substituted have one or more, preferably one or two substituents independently selected from alkyl, alkoxy, halogen, trifluoromethyl, cyano, morpholinyl and pyrrolidinyl. Preferred examples of heterocyclyl and substituted heterocyclyl are pyridinyl, pyrrolidinyl, piperidinyl, morpholinyl, thiophenyl, tetrahydrofuranyl and furyl, wherein each of these rings is optionally substituted with one or more, preferably one or two substituents selected from alkyl, alkoxy, halogen, trifluoromethyl and cyano. Particularly preferred examples are pyrrolidinyl, pyridinyl or furyl, wherein each of these cycles is optionally substituted with halogen or cyano, preferably fluoro, chloro or cyano.

The term "heteroaryl", alone or in combination, signifies aromatic 5- to 10-membered heterocycle which contains one or more, preferably one or two hetero atoms selected from nitrogen, oxygen and sulfur, wherein nitrogen or oxygen are preferred. If desired, it can be substituted on one or more carbon atoms by halogen, alkyl, alkoxy, cyano, haloalkyl, heterocyclyl, preferably trifluoromethyl. Preferred heteroaryl cycles are pyridinyl or thiophenyl optionally substituted by one or more, preferably one or two substituents independently selected from halogen, alkyl, alkoxy, cyano and haloalkyl, preferably trifluoromethyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two substituents with the nitrogen atom to which they are bonded together forming a ring. Amino may be, for example, —$NH_2$, methylamino, ethylamino, dimethylamino, diethylamino, methylethylamino, pyrrolidin-1-yl, or piperidino, etc., preferably amino, dimethylamino and diethylamino and particularly primary amino.

The term "halogen" signifies fluorine, chlorine, bromine or iodine and preferably fluorine, chlorine or bromine.

The term "carbonyl", alone or in combination signifies the —C(O)— group.

The term "hydroxyalkyl", alone or in combination signifies an alkyl group as defined before, wherein one or more, preferably one hydrogen atom is replaced by a hydroxy group.

The term "cyano", alone or in combination signifies the group —CN.

The term "heterocyclyloxy", alone or in combination signifies the group heterocyclyl-O—, wherein the term heterocyclyl is defined as before.

The term "acetylamino", alone or in combination signifies the group —NH—CO—$CH_3$.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates.

In the nomenclature used in the present description the ring atoms of the quinazoline ring are numbered as follows:

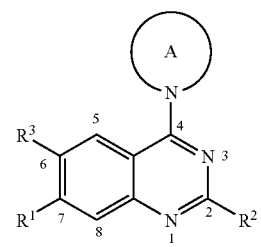

Preferred are the compounds of formula I and pharmaceutically acceptable salts thereof, particularly the compounds of formula I.

Preferred are compounds of the formula I, wherein $R^2$ is alkyl, particularly methyl.

Further preferred are compounds of formula I, wherein $R^3$ is hydrogen.

A further preferred aspect of the present invention are compounds of formula I, wherein $R^1$ is —O—$R^4$.

Further preferred are compounds of formula I, wherein $R^1$ is —N($R^5$)($R^6$).

Also preferred are compounds of formula I, wherein $R^4$ is hydrogen, aralkyl, heterocyclylalkyl or cycloalkylalkyl. Particularly preferred are those compounds of formula I, wherein $R^4$ is benzyl or pyridinylmethyl both substituted with cyano, fluoro or chloro.

Preferred are those compounds of formula I, wherein $R^1$ is —N($R^5$)($R^6$) and one of $R^5$ or $R^6$ is hydrogen and the other is selected from alkyl, cycloalkyl, cycloalkylalkyl, alkylcarbonyl, cycloalkylcarbonyl, aryl, aralkyl, arylcarbonyl, alkoxyalkyl, hydroxyalkyl, heterocyclyl, heterocyclylalkyl, heterocyclylcarbonyl, alkyl-SO$_2$—, aryl-SO$_2$—, heterocyclyl-SO$_2$— or amino-SO$_2$—.

A further preferred embodiment of the present invention are compounds according to formula I, wherein $R^5$ and $R^6$ are independently selected from hydrogen, alkyl, cycloalkylalkyl, aryl, aralkyl, heterocyclyl or heterocyclylcarbonyl. Particularly preferred are those compounds of formula I, wherein $R^5$ or $R^6$ is hydrogen and the other one is alkyl, pyridinyl, furanylcarbonyl or pyridinyl.

Also preferred are compounds of formula I, wherein A is a 5 to 7-membered saturated heterocyclic ring comprising the nitrogen atom which is attached to the quinazoline ring and, wherein the ring A is optionally substituted by one or more substituents, preferably one substituent independently selected from halogen, alkyl, alkoxy, haloalkoxy, cycloalkylalkoxy, hydroxy, amino, acetylamino, cyano, hydroxyalkyl, alkoxyalkyl, haloalkoxyalkyl and cycloalkylalkoxyalkyl. Further preferred are those compounds of formula I, wherein A is a 5 or 6-membered saturated heterocyclic ring, preferably a 5-membered saturated heterocyclic ring, comprising the nitrogen atom which is attached to the quinazoline ring and, wherein the ring A is optionally substituted by one or more substituents, preferably one substituent independently selected from halogen, alkyl, alkoxy, haloalkoxy, cycloalkylalkoxy, hydroxy, amino, acetylamino, cyano, hydroxyalkyl, alkoxyalkyl, haloalkoxyalkyl and cycloalkylalkoxyalkyl.

A further preferred embodiment of the present invention are compounds of formula I, wherein A is a 5 membered saturated heterocyclic ring comprising the nitrogen atom which is attached to the quinazoline ring and, wherein the ring A is optionally substituted by one or more substituents, preferably one independently selected from alkoxy, hydroxy or hydroxyalkyl. Particularly preferred are those compounds according to formula I, wherein A is pyrrolidinyl or pyrrolidinyl substituted with alkoxy, hydroxy or hydroxyalkyl.

Further particularly preferred are those compounds according to formula I, wherein A is pyrrolidinyl or pyrrolidinyl substituted with hydroxymethyl, methoxy or ethoxy.

Examples of preferred compounds of formula (I) are
1. 7-Benzyloxy-2-methyl-4-pyrrolidin-1-yl-quinazoline;
2. 2-Methyl-4-pyrrolidin-1-yl-quinazolin-7-ol;
3. 4-(2-Methyl-4-pyrrolidin-1-yl-quinazolin-7-yloxymethyl)-benzonitrile;
4. 7-(2-Chloro-pyridin-3-ylmethoxy)-2-methyl-4-pyrrolidin-1-yl-quinazoline;
5. 2-(2-Methyl-4-pyrrolidin-1-yl-quinazolin-7-yloxymethyl)-benzonitrile;
6. 7-(2-Fluoro-pyridin-3-ylmethoxy)-2-methyl-4-pyrrolidin-1-yl-quinazoline;
7. 5-(2-Methyl-4-pyrrolidin-1-yl-quinazolin-7-yloxymethyl)-pyridine-2-carbonitrile;
8. 7-Cyclopropylmethoxy-2-methyl-4-pyrrolidin-1-yl-quinazoline hydrochloride;
9. 4-(2-Methyl-4-pyrrolidin-1-yl-quinazolin-7-yloxy)-benzonitrile hydrochloride;
10. (S)-[1-(7-Benzyloxy-2-methyl-quinazolin-4-yl)-pyrrolidin-2-yl]-methanol;
11. (S)-4-(2-Hydroxymethyl-pyrrolidin-1-yl)-2-methyl-quinazolin-7-ol;
12. (S)-4-[4-(2-Hydroxymethyl-pyrrolidin-1-yl)-2-methyl-quinazolin-7-yloxymethyl]-benzonitrile;
13. (S)-{1-[7-(2-Chloro-pyridin-3-ylmethoxy)-2-methyl-quinazolin-4-yl]-pyrrolidin-2-yl}-methanol;
14. (S)-{1-[7-(2-Fluoro-pyridin-3-ylmethoxy)-2-methyl-quinazolin-4-yl]-pyrrolidin-2-yl}-methanol;
15. (S)-5-[4-(2-Hydroxymethyl-pyrrolidin-1-yl)-2-methyl-quinazolin-7-yloxymethyl]-pyridine-2-carbonitrile;
16. (S)-[1-(7-Cyclopropylmethoxy-2-methyl-quinazolin-4-yl)-pyrrolidin-2-yl]-methanol;
17. (S)-7-Benzyloxy-4-(3-ethoxy-pyrrolidin-1-yl)-2-methyl-quinazoline;
18. (S)-4-(3-Ethoxy-pyrrolidin-1-yl)-2-methyl-quinazolin-7-ol;
19. (S)-4-[4-(3-Ethoxy-pyrrolidin-1-yl)-2-methyl-quinazolin-7-yloxymethyl]-benzonitrile;
20. (S)-1-(7-Benzyloxy-2-methyl-quinazolin-4-yl)-pyrrolidin-3-ol;
21. (S)-4-(3-Hydroxy-pyrrolidin-1-yl)-2-methyl-quinazolin-7-ol;
22. (S)-4-[4-(3-Hydroxy-pyrrolidin-1-yl)-2-methyl-quinazolin-7-yloxymethyl]-benzonitrile hydrochloride;
23. Cyclopropylmethyl-(2-methyl-4-pyrrolidin-1-yl-quinazolin-7-yl)-amine;
24. Isobutyl-(2-methyl-4-pyrrolidin-1-yl-quinazolin-7-yl)-amine;
25. (2,2-Dimethyl-propyl)-(2-methyl-4-pyrrolidin-1-yl-quinazolin-7-yl)-amine;
26. (2-Chloro-benzyl)-(2-methyl-4-pyrrolidin-1-yl-quinazolin-7-yl)-amine;
27. (2-Methyl-benzyl)-(2-methyl-4-pyrrolidin-1-yl-quinazolin-7-yl)-amine;
28. 4-(2-Methyl-4-pyrrolidin-1-yl-quinazolin-7-ylamino)-benzonitrile;
29. (4-Fluoro-phenyl)-(2-methyl-4-pyrrolidin-1-yl-quinazolin-7-yl)-amine;
30. (2-Methyl-4-pyrrolidin-1-yl-quinazolin-7-yl)-pyridin-3-yl-amine;
31. Furan-2-carboxylic acid (2-methyl-4-pyrrolidin-1-yl-quinazolin-7-yl)-amide;
32. (S)-[4-(3-Ethoxy-pyrrolidin-1-yl)-2-methyl-quinazolin-7-yl]-pyridin-3-yl-amine;
33. (S)-[4-(3-Ethoxy-pyrrolidin-1-yl)-2-methyl-quinazolin-7-yl]-(4-fluoro-phenyl)-amine; and
34. (S)-[4-(3-Methoxy-pyrrolidin-1-yl)-2-methyl-quinazolin-7-yl]-pyridin-3-yl-amine.

Examples of particularly preferred compounds of formula (I) are
4-(2-Methyl-4-pyrrolidin-1-yl-quinazolin-7-yloxymethyl)-benzonitrile;
7-(2-Chloro-pyridin-3-ylmethoxy)-2-methyl-4-pyrrolidin-1-yl-quinazoline;

7-(2-Fluoro-pyridin-3-ylmethoxy)-2-methyl-4-pyrrolidin-1-yl-quinazoline;
(S)-{1-[7-(2-Chloro-pyridin-3-ylmethoxy)-2-methyl-quinazolin-4-yl]-pyrrolidin-2-yl}-methanol;
(S)-4-[4-(3-Ethoxy-pyrrolidin-1-yl)-2-methyl-quinazolin-7-yloxymethyl]-benzonitrile;
Isobutyl-(2-methyl-4-pyrrolidin-1-yl-quinazolin-7-yl)-amine;
(2-Methyl-4-pyrrolidin-1-yl-quinazolin-7-yl)-pyridin-3-yl-amine;
Furan-2-carboxylic acid (2-methyl-4-pyrrolidin-1-yl-quinazolin-7-yl)-amide;
(S)-[4-(3-Ethoxy-pyrrolidin-1-yl)-2-methyl-quinazolin-7-yl]-pyridin-3-yl-amine; and
(S)-[4-(3-Methoxy-pyrrolidin-1-yl)-2-methyl-quinazolin-7-yl]-pyridin-3-yl-amine.

The substituents and indices used in the following description of the processes have the significance given above unless indicated to the contrary.

Compounds of general formula Ia, whereas $R^1$ equals $N(R^5)(R^6)$, can be obtained according to scheme 1 from compounds of formula IIa (Hal means Cl, Br or I), comprising $R^2$ and $R^3$ substituents and A according to the above definition, by a Pd catalyzed Buchwald-type coupling reaction from the corresponding amines, amides or sulfonamides with, for example, Pd(OAc)$_2$ as catalyst, BINAP (2,2bis(dipenylphosphino)-1,1-binaphthyl) or Xanthphos as chelating phosphine ligand and with NaOtBu or cesium carbonate as a base—in a solvent such as toluene or dioxane, and at elevated temperature (S. L. Buchwald in: J. Am. Chem. Soc., 1996, p10333; Acc. Chem. Res. 1998, p 805; Org Lett., 2000, 2, p1104).

Alternatively, the couplings can be achieved via an Ullmann-type reaction with, Cu(I) chloride or Cu(I) iodide in a solvent such as dioxane or DMF, in analogy to procedures described by S. L. Buchwald (J. Am. Chem. Soc., 2001, p7727).

Scheme 1

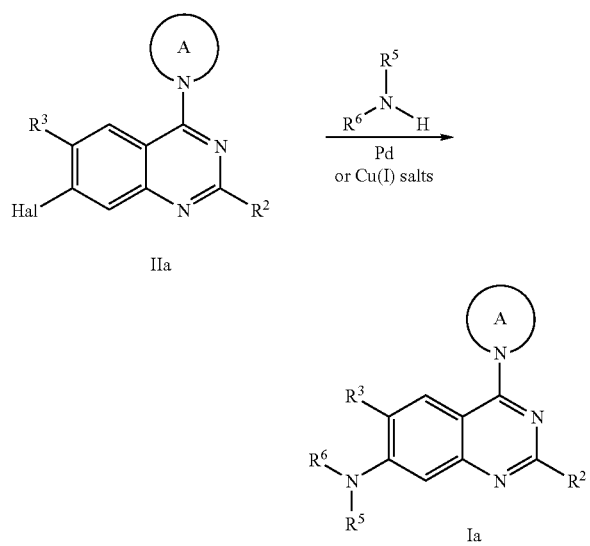

Alternatively, compounds of formula Ia can be obtained from IIb, according to scheme 2, by an appropriate sequence of alkylation reactions with corresponding alkyl halides in the presence of a base such as sodium hydride in THF or DMSO. An alternative consists of using Buchwald-type Pd catalyzed C/N bond formation reactions or Ullmann-type couplings with aryl and heteroaryl halogenides as discussed above—for the derivatives with $R^5$, $R^6$ equaling aryl and heteroaryl. Compounds with $R^5$, $R^6$ equaling alkylcarbonyl, arylcarbonyl, heterocylylcarbonyl, aryl-, heteroaryl-, alkyl- or amino sulfonyl can prepared from IIb via an acylation (or sulfonation) reaction from corresponding acyl halides or sulfonyl chlorides in the presence of a base such as DMAP or triethyl amine and in solvents such as THF or DMF or methylene chloride. Hal in scheme 2 means chloro, bromo or iodo. For the compounds with $R^2$ equaling amino, prior to performing the reactions described above, protection of amino might be preferable. This can, for example, be achieved by amino acylation (for example with acetyl chloride) of a suited intermediate of the reaction sequence shown below, using standard conditions known in the art. The acyl group can later be removed by hydrolysis.

Scheme 2

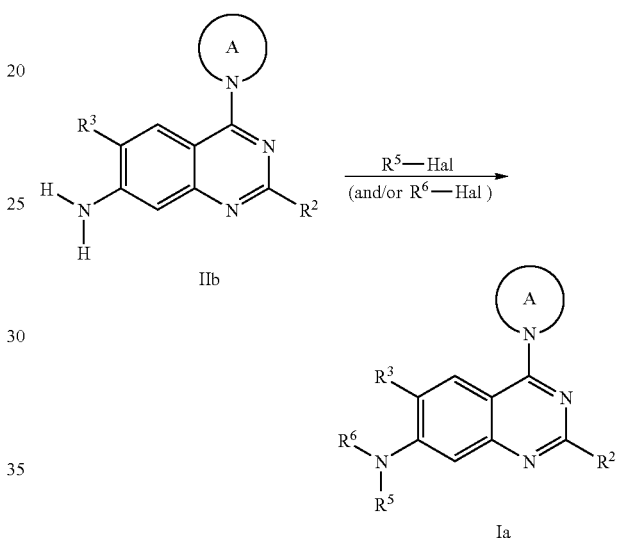

Compounds of general formula Ib, with $R^1$ equaling $O-R^4$, can be obtained according to scheme 3 from compounds of formula IIc, comprising $R^2$ and $R^3$ substituents according to the above definition, by alkylation or sulfonation reactions from the corresponding halides or sulfonyl chlorides with, e.g. K$_2$CO$_3$ as a base and in a suited solvent such as DMF. The reactions to introduce $R^4$ can also be applied to suited intermediates of the reaction sequence described below, prior to implementation of the substituents in 4-quinoline position by inverting the reaction steps.

Scheme 3

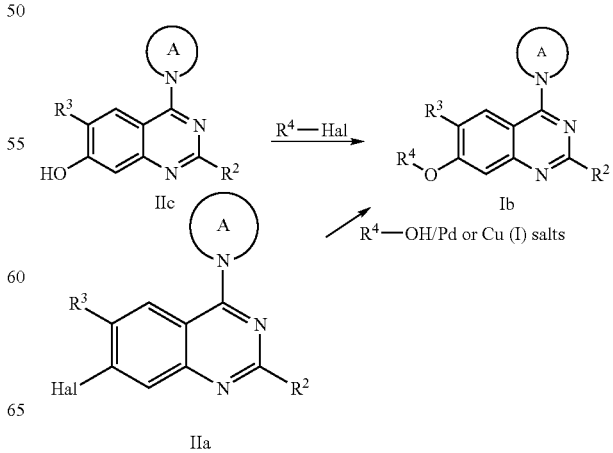

Compounds of general formula Ib can also be prepared according to scheme 3 from compounds of formula IIa on reaction with appropriate alcohols R⁴OH in a Pd catalyzed C/O bond forming reaction, with, for example, $Pd(OAc)_2$, 2-(di-t-butylphosphino)-1,1'-binaphthyl as ligand, $Cs_2CO_3$ as base in toluene as solvent (in analogy to: S. L Buchwald, J. Am. Chem. Soc., 2001, 123, p10770). Alternatively, the coupling can be performed by Ullmann-type reaction with, for example, Cu(I) iodide as catalyst, in the presence of catalytic amounts of 1,10-phenanthroline, with $Cs_2CO_3$ as base and in toluene as solvent, in analogy to a method described recently by S. L. Buchwald (Org. Letters, 2002, p973).

reflux, optionally in the presence of N,N-dimethylaniline, a standard method known in the literature. Subsequent reaction with corresponding amines as defined above, either using a large excess of amine without solvent or on reaction with a 2-fold access in a suited solvent such as N-methyl pyrrolidone, xylene, ethanol or THF, optionally in the presence of catalytic amounts of NaI and with pyridine as a base, gives compounds of formula IIa, and IIc (after cleavage of the benzyl ether group by hydrogenation). Compounds of formula IIb can be obtained from IIa by a palladium catalyzed cross coupling reaction with benzophenone imine and subsequent hydrolysis, a method described by S. L. Buchwald (Tetrahedron Lett.: 1997, p 6367).

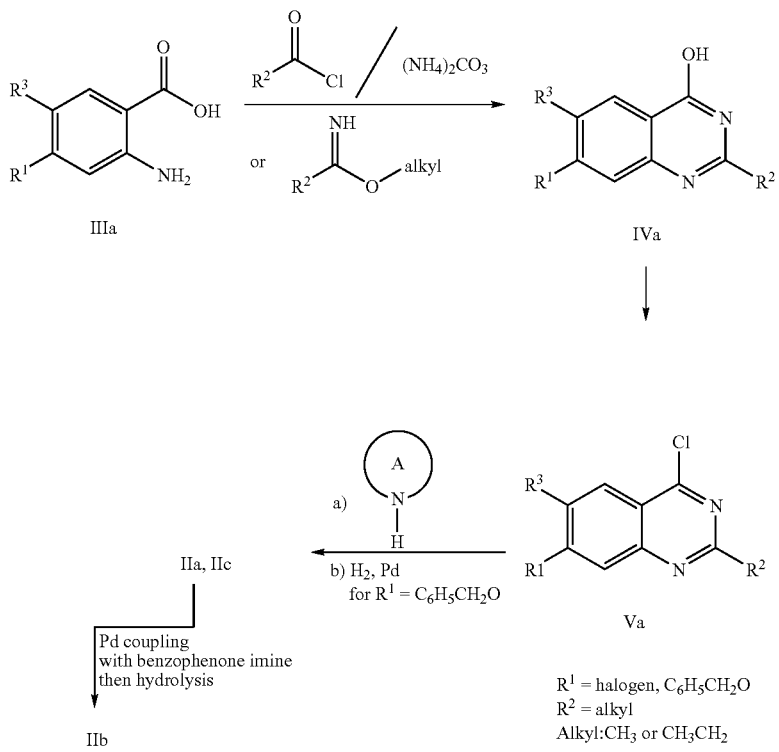

The preparation of the compounds of formula IIa–c is outlined in schemes 4 and 5:

For compounds with $R^2$ equaling alkyl, the synthesis starts, according to scheme 4, with appropriate 2-amino benzoic acid derivatives IIIa that are either known in the literature or can be prepared by standard procedures. The subsequent reaction steps are in analogy to procedures essentially known in the art. Thus, on reaction of compounds of formula IIIa with alkyl carboxylic acid chlorides in the presence of a tertiary amine such as triethyl amine, with catalytic amounts of 4-dimethylaminopyridine (DMAP), and in the presence of ammonium carbonate, in DMF the corresponding quinazolines of formula IVa are obtained. Alternatively, compounds of formula IVa can be obtained from IIIa on reaction with corresponding alkyl imino esters, in a solvent such as methanol and in the presence of a base such as triethyl amine at reflux temperature. The transformation to the corresponding chloro quinazoline derivatives of formula Va is performed on treatment with $POCl_3$ under Compounds of formula IIa–c, with $R^2$ equaling $NH_2$ or amino, can be prepared according to scheme 5. Thus, 2-amino benzoic acid esters of formula IIIb (or analogous derivatives) can be converted to the quinazolines of formula IVb on treatment with chloroformamidine hydrochloride in DMSO as a solvent (for an analogous reaction: J. Med. Chem., 1990, p2045) or on reacting with cyanamide in the presence of HCl and subsequent treatment with a base such as NaOH (for an analogous reaction: J. Med. Chem., 2000, p4288). The $NH_2$ group of compounds of formula IVb can then be selectively alkylated on reaction with appropriate alkyl halides as known in the art to give compounds of formula IVc. Alternatively, compounds of formula IVc can be prepared from IIIb and substituted cyanamides or chloroamidines according to scheme 5. The conversion of compounds of formula IVb and IVc to compounds of general formula IIa–c, with $R^2$ equaling amino, is following the sequence outlined in Scheme 4.

Scheme 5

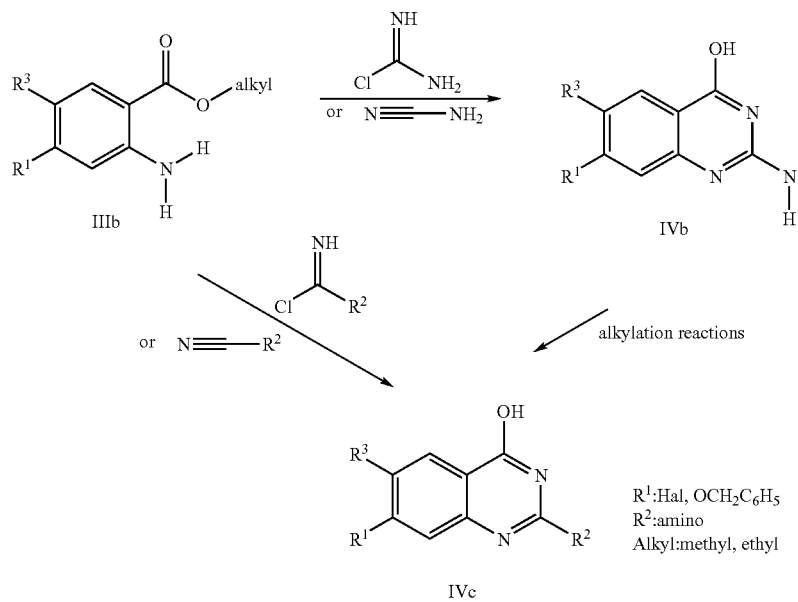

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula I by treatment with physiologically compatible bases.

The conversion of compounds of formula I into pharmaceutically acceptable esters or amides can be carried out e.g. by treatment of suited amino or hydroxyl groups present in the molecules with an carboxylic acid such as acetic acid, with a condensating reagent such as benzotriazol-1-yloxytris(dimethylamino)phosphonium hexafluorophosphate (BOP) or N,N-dicylohexylcarbodiimide (DCCI) to produce the carboxylic ester or carboxylic amide.

A preferred process for the preparation of a compound of formula I comprising one of the following reactions a) reaction of a compound according to formula IIa in the presence of $R^6(R^5)NH$ in order to obtain a compound according to formula Ia

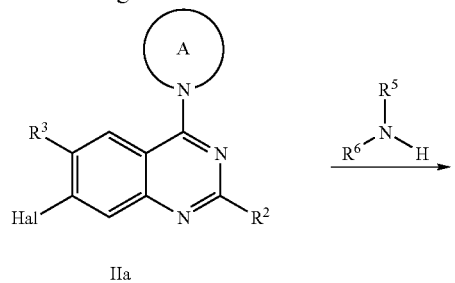

-continued

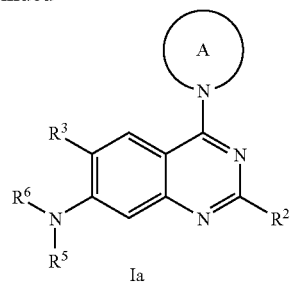

wherein $R^2$, $R^3$, $R^5$, $R^6$ and A are defined as before and Hal means chloro, bromo or iodo;

b) reaction of a compound according to formula IIb in the presence of $R^5$-Hal and/or $R^6$-Hal in order to obtain a compound according to formula Ia

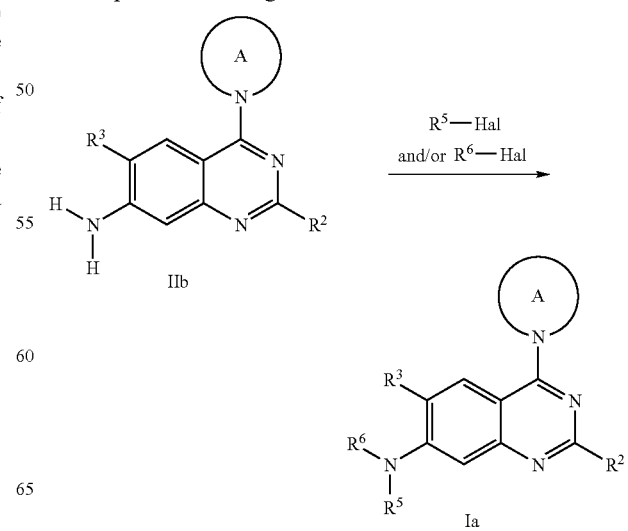

wherein $R^2$, $R^3$, $R^5$, $R^6$ and A are defined as before and Hal means chloro, bromo or iodo;

c) reaction of a compound according to formula IIc in the presence of $R^4$-Hal in order to obtain a compound according to formula Ib

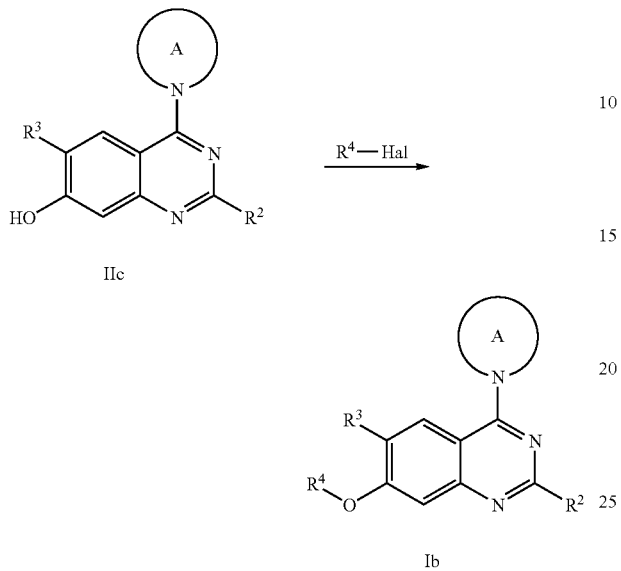

wherein $R^2$, $R^3$, $R^4$ and A are defined as before and Hal means chloro, bromo or iodo;

d) reaction of a compound according to formula IIa in the presence of $R^4$—OH in order to obtain a compound according to formula Ib

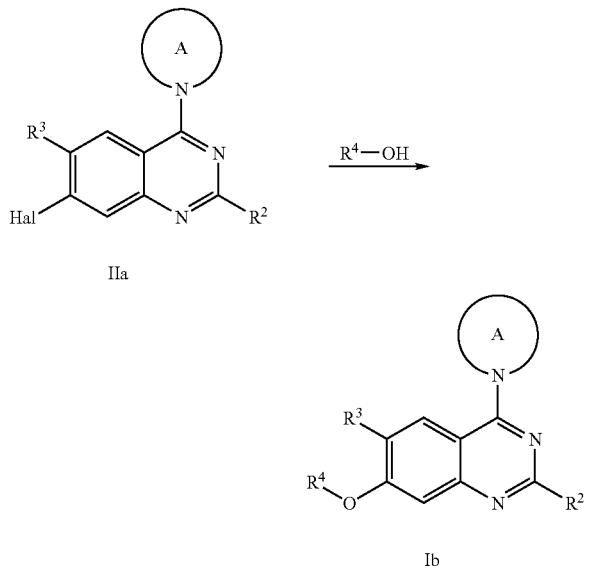

wherein $R^2$, $R^3$, $R^4$ and A are defined as before and Hal means chloro, bromo or iodo.

Preferred intermediates are:
7-Benzyloxy-4-chloro-2-methyl-quinazoline;
7-Bromo-2-methyl-4-pyrrolidin-1-yl-quinazoline;
(S)-7-Bromo-4-(3-ethoxy-pyrrolidin-1-yl)-2-methyl-quinazoline and
(S)-7-bromo-4-(3-methoxy-pyrrolidin-1-yl)-2-methyl-quinazoline.

The compounds of formula I described above for use as therapeutically active substances are a further object of the invention.

Also an object of the invention are compounds described above for the production of medicaments for the prophylaxis and therapy of illnesses which are caused by disorders associated with the NPY receptor, particularly for the production of medicaments for the prophylaxis and therapy of arthritis, cardiovascular diseases, diabetes, renal failure and particularly eating disorders and obesity.

Likewise an object of the invention are pharmaceutical compositions containing a compound of formula I described above and a therapeutically inert carrier.

An object of the invention is also the use of the compounds described above for the production of medicaments, particularly for the treatment and prophylaxis of arthritis, cardiovascular diseases, diabetes, renal failure and particularly eating disorders and obesity.

A further object of the invention comprises compounds which are manufactured according to one of the described processes.

A further object of the invention is a method for the treatment and prophylaxis of arthritis, cardiovascular diseases, diabetes, renal failure and particularly eating disorders and obesity whereby an effective amount of a compound described above is administered.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

Also an object of the invention are compounds described above for the production of medicaments for the prophylaxis and therapy of alcoholism.

A further object of the invention is a method for the treatment and prophylaxis of alcoholism.

Assay Procedures

Cloning of Mouse NPY5 Receptor cDNAs

The full-length cDNA encoding the mouse NPY5 (mNPY5) receptor was amplified from mouse brain cDNA using specific primers, designed based on the published sequence, and Pfu DNA-Polymerase. The amplification product was subcloned into the mammalian expression vector pcDNA3 using Eco RI and XhoI restriction sites. Positive clones were sequenced and one clone, encoding the published sequence was selected for generation of stable cell clones.

Stable Transfection

Human embryonic kidney 293 (HEK293) cells were transfected with 10 μg mNPY5 DNA using the lipofectamine reagent. Two days after transfection, geneticin selection (1 mg/ml) was initiated and several stable clones were isolated. One clone was further used for pharmacological characterization.

Radioligand Competition Binding

Human embryonic kidney 293 cells (HEK293), expressing recombinant mouse NPY5-receptor (mNPY5) were broken by three freeze/thawing cycles in hypotonic Tris buffer (5 mM, pH 7.4, 1 mM $MgCl_2$), homogenized and centrifuged at 72,000×g for 15 min. The pellet was washed twice with 75 mM Tris buffer, pH 7.4, containing 25 mM $MgCl_2$ and 250 mM sucrose, 0.1 mM phenylmethylsulfonylfluoride and 0.1 mM 1,10-pheneanthrolin, resuspended in the same buffer and stored in aliquots at −80° C. Protein was determined according to the method of Lowry using bovine serum albumine (BSA) as a standard.

Radioligand competition binding assays were performed in 250 μl 25 mM Hepes buffer (pH 7.4, 2.5 mM $CaCl_2$, 1 mM $MgCl_2$, 1% bovine serum albumine, and 0.01% $NaN_3$ containing 5 μg protein, 100 pM [$^{125}$I]labeled peptide YY (PYY) and 10 μL DMSO containing increasing amounts of unlabelled test compounds. After incubation for 1 h at 22° C., bound and free ligand are separated by filtration over glass fibre filters. Non specific binding is assessed in the presence of 1 μM unlabelled PYY. Specific binding is defined as the difference between total binding and non specific binding. $IC_{50}$ values are defined as the concentration of antagonist that displaces 50% of the binding of [$^{125}$I] labeled neuropeptide Y. It is determined by linear regression analysis after logit/log transformation of the binding data.

Results obtained in the foregoing test using representative compounds of the invention as the test compounds are shown in the following table:

| Compound | NPY5-R (mouse) $IC_{50}$ (nM) |
|---|---|
| 3 | 9 |
| 24 | 3 |

Preferred compounds as described above have $IC_{50}$ values below 1000 nM; more preferred compounds have $IC_{50}$ values below 100 nM, particularly below 10 nM. Most preferred compounds have $IC_{50}$ values below 2 nM. These results have been obtained by using the foregoing test.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragees, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, water, polyols, saccharose, invert sugar, glucose, etc. Suitable adjuvants for injection solutions are, for example, water, alcohols, polyols, glycerol, vegetable oils, etc. Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1–3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1 a) A solution of 0.44 g (1.55 mmol) of 7-benzyloxy-4-chloro-2-methyl-quinazoline in 1.9 ml (23.2 mmol) of pyrrolidine was heated at reflux for 17 h under argon. The reaction mixture was concentrated in vacuo, the residue applied to a silica gel column with $CH_2Cl_2$/MeOH (98:2 to 95:5) as eluant. Combination of the purified fractions and concentration in vacuo gave 0.31 g (58.7%) of the desired of 7-benzyloxy-2-methyl-4-pyrrolidin-1-yl-quinazoline as a viscous yellow oil. ISP mass spectrum, m/e: 320.4 (M+1 calculated for $C_{20}H_{21}N_3O$:320).

Preparation of the Starting Material b) A suspension of 1.1 g (5.64 mmol) of 2-acetylamino-4-hydroxy-benzoic acid (preparation: Recl. Trav. Chim. Pays-Bas, 72, p195, 1953), 1.6 ml (13.53 mmol) of benzyl chloride, 3.9 g (28.18 mmol) of potassium carbonate in DMF (15 ml) was stirred at 80° C. for 17 h under argon. The reaction mixture was concentrated in vacuo and partitioned between $CH_2Cl_2$ and water. The layers were separated, the aqueous layer once extracted with $CH_2Cl_2$, the organic layers combined, washed with brine, dried over $MgSO_4$ and concentrated in vacuo, to give 1.89 g (85.75%) of the desired 2-acetylamino-4-benzyloxy-benzoic acid benzyl ester as an off-white solid. ISP mass spectrum, m/e: 376.5 (M+1 calculated for $C_{23}H_{21}NO_4$: 375.42).

c) A suspension of 1.87 g (4.98 mmol) of 2-acetylamino-4-benzyloxy-benzoic acid benzyl ester in EtOH (20 ml) was treated with 1N NaOH (20–30 ml) and stirred at 95° C.–130° C. (oil bath temperature) until completion of the reaction according to TLC and NMR analysis (reaction time about 34 h). The reaction mixture was cooled to RT, brought to pH 6 on addition of 1N aqueous HCl, the precipitate that formed was filtered off by suction and dried in a high vacuum to give 1.19 g (91.7%) of the desired 2-amino-4-benzyloxy-benzoic acid as an off-white solid. ISP mass spectrum, m/e: 242.2 (M+1 calculated for $C_{14}H_{13}NO_3$: 242).

d) To a solution of 0.695 g (5.62 mmol) of ethyl acetoamidate hydrochloride in MeOH (16 ml) were added under stirring at RT 0.82 ml (5.86 mmol) of triethyl amine and 5 minutes later 1.14 g (4.69 mmol) of 2-amino-4-benzyloxy-benzoic acid. The reaction mixture was heated at reflux for 5 h, cooled to RT, the precipitate that had formed was filtered off by suction and dried in a high vacuum to give 0.9 g (69.4%) of the desired 7-benzyloxy-2-methyl-1H-quinazolin-4-one as an white solid. ISP mass spectrum, m/e: 267.3 (M+1 calculated for $C_{16}H_{14}N_2O_2$: 267).

e) A suspension of 0.9 g (3.38 mmol) of 7-benzyloxy-2-methyl-1H-quinazolin-4-one in $POCl_3$ (4.6 ml, 50 mmol) were heated at reflux for 1.5 h. The reaction mixture was then concentrated in vacuo, the residue was partitioned between $CH_2Cl_2$ and cold diluted $NaHCO_3$ (pH 7–8). The layers were separated and the aqueous layer twice extracted with $CH_2Cl_2$. The combined organic layers washed with saturated $NaHCO_3$, brine and then dried over $Mg_2SO_4$. The solvent was removed in vacuo give 0.45 g (47.2%) of crude 7-benzyloxy-4-chloro-2-methyl-quinazoline as a dark red waxy solid which was used directly in the next step without further purification. Rf: 0.9 ($CH_2Cl_2$/MeOH: 9/1; starting material with Rf: 0.7).

Example 2

A suspension of 0.255 g (0.8 mmol) of 7-benzyloxy-2-methyl-4-pyrrolidin-1-yl-quinazoline, product of example 1, in MeOH (5 ml) was treated with 75 mg of palladium on charcoal (10%) and then hydrogenated at RT for 2 h until HPLC analysis indicated completion of the reaction. The catalyst was filtered off and the filtrate concentrated in vacuo. The solid that precipitated was collected by filtration and dried in a high vacuum to give 0.19 g (98%) of 2-methyl-4-pyrrolidin-1-yl-quinoazlin-7-ol as a yellow solid. ISP mass spectrum, m/e: 230.2 (M+1 calculated for $C_{13}H_{15}N_3O$: 230).

Example 3

A mixture of 90 mg (0.4 mmol) of 2-methyl-4-pyrrolidin-1-yl-quinoazlin-7-ol, product of example 2, 130 mg (0.94 mmol) of potassium carbonate and 92 mg (0.47 mmol) of 4-(bromomethyl)-benzonitrile was heated in DMF (4 ml) at 100° C. for 2.5 h under an argon atmosphere. The mixture was cooled to RT, poured into ether (40 ml) and stirred for 5 minutes. The precipitate that formed was filtered off by suction, washed with water then ether and dried in a high vacuum to give 108 mg (75.2%) of 4-(2-methyl-4-pyrrolidin-1-yl-quinazolin-7-yloxymethyl)-benzonitrile as a light yellow solid. ISP mass spectrum, m/e: 345.4 (M+1 calculated for $C_{21}H_{20}N_4O$: 345).

Example 4

In analogy to example 3 there was prepared: on reaction of 2-methyl-4-pyrrolidin-1-yl-quinoazlin-7-ol with 2-chloro-3-chloromethyl-pyridine, 7-(2-chloro-pyridin-3-ylmethoxy)-2-methyl-4-pyrrolidin-1-yl-quinazoline as a light brown solid. ISP mass spectrum, m/e: 355.3 (M+1 calculated for $C_{19}H_{19}ClN_4O$: 355).

Example 5

In analogy to example 3 there was prepared: on reaction of 2-methyl-4-pyrrolidin-1-yl-quinoazlin-7-ol with 2-bromomethyl benzonitrile, 2-(2-methyl-4-pyrrolidin-1-yl-quinazolin-7-yloxymethyl)-benzonitrile as an off-white solid. ISP mass spectrum, m/e: 345.4 (M+1 calculated for $C_{21}H_{20}N_4O$: 345).

Example 6

In analogy to example 3 there was prepared: on reaction of 2-methyl-4-pyrrolidin-1-yl-quinoazlin-7-ol with 3-chloromethyl-2-fluoro-pyridine, 7-(2-fluoro-pyridin-3-ylmethoxy)-2-methyl-4-pyrrolidin-1-yl-quinazoline as a light brown solid. ISP mass spectrum, m/e: 339.3 (M+1 calculated for $C_{19}H_{19}FN_4O$: 339).

Example 7

In analogy to example 3 there was prepared: on reaction of 2-methyl-4-pyrrolidin-1-yl-quinazolin-7-ol with 5-chloromethyl-pyridine-2-carbonitrile, 5-(2-methyl-4-pyrrolidin-1-yl-quinazolin-7-yloxymethyl)-pyridine-2-carbonitrile as light brown solid. ISP mass spectrum, m/e: 346.4 (M+1 calculated for $C_{20}H_{19}N_5O$: 346).

Example 8

In analogy to example 3 (and isolation of the product as hydrochloride), there was obtained: on reaction of 2-methyl-4-pyrrolidin-1-yl-quinazolin-7-ol with cyclopropylmethyl bromide, 7-cyclopropylmethoxy-2-methyl-4-pyrrolidin-1-yl-quinazoline hydrochloride as a white solid. ISP mass spectrum, m/e: 284.2 (M+1 calculated for $C_{17}H_{21}N_3O$: 284).

Example 9

In analogy to example 3 (and isolation of the product as hydrochloride) there was prepared: on reaction of 2-methyl-4-pyrrolidin-1-yl-quinazolin-7-ol with 4-bromobenzonitrile, 4-(2-methyl-4-pyrrolidin-1-yl-quinazolin-7-yloxy)-benzonitrile as a white solid. ISP mass spectrum, m/e 331.3 (M+1 calculated for $C_{20}H_{18}N_4O$: 331).

Example 10

In analogy to example 1, on reaction of 7-benzyloxy-4-chloro-2-methyl-quinazoline, with an excess of (S)-2-(hydroxymethyl)pyrrolidine (2,5 mole-equivalents) in 1-methyl-2-pyrrolidone as solvent at 100° C., there was obtained: (S)-[1-(7-benzyloxy-2-methyl-quinoazlin-4-yl)-pyrrolidin-2-yl]-methanol as an light brown oil. ISP mass spectrum, m/e: 350.5 (M+1 calculated for $C_{21}H_{23}N_3O_2$: 350).

Example 11

In analogy to example 2, on hydrogenation of (S)-[1-(7-benzyloxy-2-methyl-quinazolin-4-yl)-pyrrolidin-2-yl]-methanol, product of example 10, with Pd on charcoal (10%) in MeOH, there was obtained: (S)-4-(2-hydroxymethyl-pyrrolidin-1-yl)-2-methyl-quinoazlin-7-ol as a viscous light yellow oil. ISP mass spectrum, m/e: 260.3 (M+1 calculated for $C_{14}H_{17}N_3O_2$: 260).

Example 12

In analogy to example 3, on reaction of (S)-4-(2-hydroxymethyl-pyrrolidin-1-yl)-2-methyl-quinazolin-7-ol, product of example 11, with 4-bromomethyl-benzonitrile there was obtained: (S)-4-[4-(2-hydroxymethyl-pyrrolidin-1-yl)-2-methyl-quinazolin-7-yloxymethyl]-benzonitrile as a light yellow foam. ISP mass spectrum, m/e: 375.4 (M+1 calculated for $C_{22}H_{22}N_4O_2$: 375).

Example 13

In analogy to example 3, on reaction of (S)-4-(2-hydroxymethyl-pyrrolidin-1-yl)-2-methyl-quinoazlin-7-ol product of example 11, with 2-chloro-3-chloromethyl-pyridine hydrochloride there was obtained: (S)-{1-[7-(2-chloro-pyridin-3-ylmethoxy)-2-methyl-quinazolin-4-yl]-pyrrolidin-2-yl}-methanol as an off-white solid. ISP mass spectrum, m/e: 385.3 M+1 calculated for $C_{20}H_{21}ClN_4O_2$: 385).

Example 14

In analogy to example 3, on reaction of (S)-4-(2-hydroxymethyl-pyrrolidin-1-yl)-2-methyl-quinazolin-7-ol, product of example 11, with 2-fluoro-3-chloromethyl-pyridine hydrochloride there was obtained: (S)-{1-[7-(2-fluoro-pyridin-3-ylmethoxy)-2-methyl-quinazolin-4-yl]-pyrrolidin-2-yl}-methanol as a white solid. ISP mass spectrum, m/e: 369.4 (M+1 calculated for $C_{20}H_{21}FN_4O_2$: 369).

Example 15

In analogy to example 3, on reaction of (S)-4-(2-hydroxymethyl-pyrrolidin-1-yl)-2-methyl-quinazolin-7-ol, product of example 11, with 5-chloromethyl-pyridine-2-carbonitrile, there was obtained: (S)-5-[4-(2-hydroxymethyl-pyrrolidin-1-yl)-2-methyl-quinazolin-7-yloxymethyl]-pyridine-2-carbonitrile as a white solid. ISP mass spectrum, m/e: 376.4 (M+1 calculated for $C_{21}H_{21}N_5O_2$: 376).

Example 16

In analogy to example 3, on reaction of (S)-4-(2-hydroxymethyl-pyrrolidin-1-yl)-2-methyl-quinazolin-7-ol product of example 11, with cyclopropylmethyl bromide there was obtained: (S)-[1-(7-cyclopropylmethoxy-2-methyl-quinazolin-4-yl)-pyrrolidin-2-yl]-methanol as a white solid. ISP mass spectrum, m/e: 314.4 (M+1 calculated for $C_{18}H_{23}FN_3O_2$: 314).

Example 17

In analogy to example 1, on reaction of 7-benzyloxy-4-chloro-2-methyl-quinazoline, with an excess of (S)-3-ethoxy-pyrrolidine (2,5 mole-equivalents) in 1-methyl-2-pyrrolidone as solvent at 100° C., there was obtained: (S)-7-benzyloxy-4-(3-ethoxy-pyrrolidin-1-yl)-2-methyl-quinazoline as a yellow solid. ISP mass spectrum, m/e: 364.3 (M+1 calculated for $C_{22}H_{25}N_3O_2$: 364).

Example 18

In analogy to example 2, on hydrogenation of (S)-7-benzyloxy-4-(3-ethoxy-pyrrolidin-1-yl)-2-methyl-quinazoline, product of example 17, with Pd on charcoal (10%) in MeOH, there was obtained: (S)-4-(3-ethoxy-pyrrolidin-1-yl)-2-methyl-quinazolin-7-ol as a viscous light yellow solid. ISP mass spectrum, m/e: 274.3 (M+1 calculated for $C_{15}H_{19}N_3O_2$: 274).

Example 19

In analogy to example 3, on reaction (S)-4-(3-ethoxy-pyrrolidin-1-yl)-2-methyl-quinazolin-7-ol, product of example 18, with 4-bromomethyl-benzonitrile there was obtained: (S)-4-[4-(3-ethoxy-pyrrolidin-1-yl)-2-methyl-quinazolin-7-yloxymethyl]-benzonitrile as an off white solid. ISP mass spectrum, m/e: 389.3 (M+1 calculated for $C_{23}H_{24}N_4O_2$: 389).

Example 20

In analogy to example 1, on reaction of 7-benzyloxy-4-chloro-2-methyl-quinazoline, with an excess of (S)-3-hydroxy-pyrrolidine (2,5 mole-equivalents) in 1-methyl-2-pyrrolidone as solvent at 100° C., there was obtained: (S)-1-(7-benzyloxy-2-methyl-quinazolin-4-yl)-pyrrolidin-3-ol as a yellow solid. ISP mass spectrum, m/e: 336.3 (M+1 calculated for $C_{20}H_{21}N_3O_2$: 336).

Example 21

In analogy to example 2, on hydrogenation of (S)-1-(7-benzyloxy-2-methyl-quinazolin-4-yl)-pyrrolidin-3-ol, product of example 20, with Pd on charcoal (10%) in MeOH, there was obtained: (S)-4-(3-hydroxy-pyrrolidin-1-yl)-2-methyl-quinazolin-7-ol as a light brown solid. ISP mass spectrum, m/e: 246.2 (M+1 calculated for $C_{13}H_{15}N_3O_2$: 246).

Example 22

In analogy to example 3 (and with isolation of the product as hydrochloride) on reaction of (S)-1-(7-benzyloxy-2-methyl-quinazolin-4-yl)-pyrrolidin-3-ol, product of example 21, with 4-bromomethyl-benzonitrile there was obtained: (S)-4-[4-(3-hydroxy-pyrrolidin-1-yl)-2-methyl-quinolin-7-yloxymethyl]-benzonitrile hydrochloride as an off white solid. ISP mass spectrum, m/e: 361.3 (M+1 calculated for $C_{21}H_{20}N_4O_2$: 361).

Example 23 a) A suspension of 0.15 g (0.513 mmol) of 7-bromo-2-methyl-4-pyrrolidin-1-yl-quinazoline, 21.3 mg (0.034 mmol) racemic BINAP, 3.8 mg (0.017 mmol) of palladium (II)acetate and 65.8 mg (0.685 mmol) of sodium tert-butylate in toluene (8 ml) was treated at RT with 0.365 g (5.13 mmol) of aminomethyl cyclopropane and then heated to reflux under an argon atmosphere for 20 h. The reaction mixture was then filtered by suction over fiberglass filter paper and the filtrate was partitioned between EtOAc and water. The layers were separated, the organic layer dried over sodium sulphate and concentrated in vacuo. The residue was applied to silica gel column with $CH_2Cl_2$/MeOH/$NH_4OH$ (10:1:0.2) as eluent. Combination of the purified fractions and concentration in vacuo gave 68 mg (46.9%) of the desired cyclopropylmethyl-(2-methyl-4-pyrrolidin-1-yl-quinazolin-7-yl)-amine as brown viscous oil. ISP mass spectrum, m/e: 283.2 (M+1 calculated for $C_{17}H_{22}N_4$: 283).

Preparation of the Starting Material b) To a solution of 1 g (4.63 mmol) 4-bromoanthranilic acid (J. Org. Chem. 1997, 62, 1240–1256), 50 mg (0.417 mmol) of 4-(dimethylamino)pyridine and 2.58 ml (18.5 mml) of triethylamine in dry DMF (5 ml) was added dropwise 0.79 ml (11.1 mmol) of acetylchloride at 3° C. for 20 min. in an ice-water bath under argon. The reaction mixture was heated at 90° C. for 3 h. and 1.32 g (13.89 mmol) of ammonium carbonate were added portionwise over 10 min., and the mixture was stirred at the same temperature for 1 h. After cooling, the mixture was poured into water and the precipitate filtered, washed with water and dried in vacuo to give 1.1 g (99.4%) of 7-bromo-2-methyl-3H-quinazolin-4-one as a light-brown solid. Mp. >191° C. (dec.). EI mass spectrum, m/e: 240 (M calculated for $C_9H_7BrN_2O$: 240).

c) A suspension of 0.45 g (1.87 mmol) of 7-bromo-2-methyl-3H-quinazolin-4-one in 0.48 ml N,N-dimethylaniline was treated with 1.41 ml (15.4 mmol) phosphorous oxychloride and heated at 60° C. for 2 h. The reaction mixture was evaporated in vacuo and the residue taken up in 20 ml water, neutralized with 10 ml saturated aqueous sodium bicarbonate and twice extracted with 25 ml dichloromethane. The organic layer is washed with 25 ml water, 25 ml brine, dried over magnesium sulfate and evaporated in vacuo. The residue is purified by chromatography on silica gel with heptane/ethylacetate (2:1) to give 0.29 g (59%) of 7-bromo-4-chloro-2-methyl-quinazoline as an orange solid. Mp. >82° C. EI mass spectrum, m/e: 258 (M calculated for $C_9H_6BrClN_2$: 258).

d) A solution of 0.8 g (3.1 mmol) of 7-bromo-4-chloro-2-methyl-quinazoline in 2 ml of pyrrolidine was heated at reflux for 12 h. The reaction mixture was concentrated in vacuo, the residue applied to a silica gel column with $CH_2Cl_2$/MeOH (95:5) as eluant. Combination of the purified fractions and concentration in vacuo gave 1 g (100%) of the desired of 7-bromo-2-methyl-4-pyrrolidin-1-yl-quinazoline as a yellow solid. Mp. 120–122° C. ISP mass spectrum, m/e: 292.2 (M+1 calculated for $C_{13}H_{14}BrN_3$: 292).

Example 24

In analogy to example 23, on reaction of 7-bromo-2-methyl-4-pyrrolidin-1-yl-quinazoline with isobutylamine there was obtained: isobutyl-(2-methyl-4-pyrrolidin-1-yl-quinazolin-7-yl)-amine as an light brown amorphous solid. ISP mass spectrum, m/e: 285.3 (M+1 calculated for $C_{17}H_{24}N_4$: 284.4).

Example 25

In analogy to example 23, on reaction of 7-bromo-2-methyl-4-pyrrolidin-1-yl-quinazoline with 2,2-dimetylpropylamine there was obtained: (2,2-dimethyl-propyl)-(2-methyl-4-pyrrolidin-1-yl-quinazolin-7-yl)-amine as brown foam. ISP mass spectrum, m/e: 299.5 (M+1 calculated for $C_{18}H_{26}N_4$: 298.43).

Example 26

In analogy to example 23, on reaction of 7-bromo-2-methyl-4-pyrrolidin-1-yl-quinoazoline with 2-chloro-benzylamine there was obtained: (2-chloro-benzyl)-(2-methyl-4-pyrrolidin-1-yl-quinazolin-7-yl)-amine as a yellow solid. ISP mass spectrum, m/e: 253.3 (M+1 calculated for $C_{20}H_{21}ClN_4$: 353).

Example 27

In analogy to example 23, on reaction of 7-bromo-2-methyl-4-pyrrolidin-1-yl-quinazoline with 2-methylbenzylamine there was obtained: (2-methyl-benzyl)-(2-methyl-4-pyrrolidin-1-yl-quinoazlin-7-yl)-amine as yellow solid. ISP mass spectrum, m/e: 333.3 (M+1 calculated for $C_{21}H_{24}N_4$: 333).

Example 28

In analogy to example 23, on reaction of 7-bromo-2-methyl-4-pyrrolidin-1-yl-quinazoline with 4-aminobenzonitrile there was obtained: 4-(2-methyl-4-pyrrolidin-1-yl-quinazolin-7-ylamino)-benzonitrile as light yellow solid. ISP mass spectrum, m/e: 330.4 (M+1 calculated for $C_{20}H_{19}N_5$: 330).

Example 29

In analogy to example 23, on reaction of 7-bromo-2-methyl-4-pyrrolidin-1-yl-quinazoline with 4-fluoro-aniline there was obtained: (4-fluoro-phenyl)-(2-methyl-4-pyrrolidin-1-yl-quinazolin-7-yl)-amine as a dark brown solid. ISP mass spectrum, m/e: 323.4 (M+1 calculated for $C_{19}H_{19}FN_4$: 323).

Example 30

In analogy to example 23, on reaction of 7-bromo-2-methyl-4-pyrrolidin-1-yl-quinazoline with 3-aminopyridine there was obtained: (2-methyl-4-pyrrolidin-1-yl-quinoazlin-7-yl)-pyridin-3-yl-amine as light brown solid. ISP mass spectrum, m/e: 306.4 (M+1 calculated for $C_{18}H_{19}N_5$: 306).

Example 31

A suspension of 0.12 g (0.41 mmol) of 7-bromo-2-methyl-4-pyrrolidin-1-yl-quinazoline, 3.9 mg (0.021 mmol) of copper (I) iodide and 0.267 g (0.82 mmol) of caesium carbonate in dioxane (5 ml) was treated at RT under argon with 4.7 mg (0.041 mmol) of trans-1,2-diaminocyclohexane and 0.18 g (1.6 mmol) of 2-furamide and then heated at reflux under argon for 20 h. The reaction mixture was partitioned between EtOAc and water, the layers were separated, the organic layer washed twice with water dried over sodium sulphate and concentrated in vacuo. The residue was applied to silica gel column with $CH_2Cl_2$/MeOH/$NH_4OH$ (9:1:0.5) as eluent. Combination of the purified fractions and concentration in vacuo gave 29 mg (22%) of the furan-2-carboxylic acid (2-methyl-4-pyrrolidin-1-yl-quinazolin-7-yl)-amide as an off white solid. ISP mass spectrum, m/e: 323.4 (M+1 calculated for $C_{18}H_{18}N_4O_2$: 323).

Example 32 a) In analogy to example 23, on reaction of (S)-7-bromo-4-(3-ethoxy-pyrrolidin-1-yl)-2-methyl-quinazoline hydrochloride with 3-aminopyridine there was obtained: (S)-[4-(3-ethoxy-pyrrolidin-1-yl)-2-methyl-quinazolin-7-yl]-pyridin-3-yl-amine as a grey solid. ISP mass spectrum, m/e: 350.5 (M+1 calculated for $C_{20}H_{23}N_5O$: 350).

Preparation of the Starting Material b) In analogy to example 23 d), on reaction of 7-bromo-4-chloro-2-methyl-quinazoline with excess (S)-3-ethoxy-pyrrolidine (2.5 mole equivalents) in 1-methyl-2-pyrrolidone as solvent and at 140° C., there was obtained: (S)-7-bromo-4-(3-ethoxy-pyrrolidin-1-yl)-2-methyl-quinazoline hydrochloride as a light yellow solid. ISP mass spectrum, m/e: 336.2 (M+1 calculated for $C_{15}H_{18}BrN_3O$: 336).

Example 33

In analogy to example 23, on reaction of (S)-7-bromo-4-(3-ethoxy-pyrrolidin-1-yl)-2-methyl-quinazoline hydrochloride, product of example 32 b), with 4-fluoroaniline there was obtained: (S)-[4-(3-ethoxy-pyrrolidin-1-yl)-2-methyl-quinazolin-7-yl]-(4-fluoro-phenyl)-amine a yellow foam. ISP mass spectrum, m/e: 367.3 (M+1 calculated for $C_{21}H_{23}FN_4O$: 367).

Example 34 a) In analogy to example 23, on reaction of (S)-7-bromo-4-(3-metoxy-pyrrolidin-1-yl)-2-methyl-quinazoline with 3-aminopyridine there was obtained: (S)-[4-(3-methoxy-pyrrolidin-1-yl)-2-methyl-quinazolin-7-yl]-pyridin-3-yl-amine as an off-white solid. ISP mass spectrum, m/e: 336.3 (M+1 calculated for $C_{19}H_{21}N_5O$: 336).

Preparation of the Starting Material b) In analogy to example 23 d), on reaction of 7-bromo-4-chloro-2-methyl-quinazoline with excess (S)-3-methoxy-pyrrolidine (2.5 mole equivalents) in 1-methyl-2-pyrrolidone as solvent and at 140° C., there was obtained: (S)-7-bromo-4-(3-methoxy-pyrrolidin-1-yl)-2-methyl-quinazoline hydrochloride as a light orange solid. ISP mass spectrum, m/e: 322.3 (M+1 calculated for $C_{14}H_{16}BrN_3O$: 322).

Example A

A compound of formula I can be used as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

What is claimed is:
1. A compound of formula I

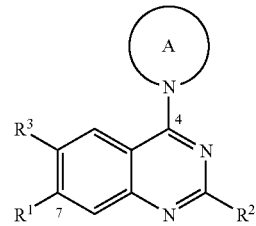

wherein
$R^1$ is $-O-R^4$ or $-N(R^5)(R^6)$;
$R^2$ is alkyl or amino;
$R^3$ is hydrogen, alkyl or halogen;
$R^4$ is hydrogen, aralkyl, substituted aralkyl, heterocyclylalkyl, substituted heterocyclylalkyl or cycloalkylalkyl;
$R^5$ and $R^6$ are independently selected from hydrogen, alkyl, cycloalkylalkyl, aryl, substituted aryl, aralkyl, substituted aralkyl, heterocyclyl, substituted heterocyclyl, heterocyclylcarbonyl or substituted heterocyclylcarbonyl;
A is a 5 to 7-membered saturated unsubstituted or substituted heterocyclic ring comprising the nitrogen atom which is attached to the quinazoline ring and optionally a second heteroatom which is selected from oxygen, sulfur or nitrogen and, wherein the ring A substituted heterocyclic ring has one or more substituents independently selected from halogen, alkyl, alkoxy, haloalkoxy, cycloalkylalkoxy, hydroxy, amino, acetylamino, cyano, hydroxyalkyl, alkoxyalkyl, haloalkoxyalkyl and cycloalkylalkoxyalkyl;
and pharmaceutically acceptable salts and esters thereof.
2. The compound according to claim 1, wherein $R^2$ is alkyl.
3. The compound according to claim 2, wherein $R^2$ is methyl.
4. The compound according to claim 1, wherein $R^3$ is hydrogen.
5. The compound according to claim 1, wherein $R^1$ is $-O-R^4$.
6. The compound according to claim 1, wherein $R^4$ is aralkyl which is benzyl, heterocyclylalkyl which is pyridinylmethyl, or aralkyl substituted with cyano, fluoro or chloro; or pyridinylmethyl substituted with cyano, fluoro or chloro.
7. The compound according to claim 1, wherein $R^1$ is $-N(R^5)(R^6)$.
8. The compound according to claim 1, wherein $R^5$ or $R^6$ is hydrogen and the other one is alkyl, pyridinyl, furanylcarbonyl or pyridinyl.
9. The compound according to claim 1, wherein A is a 5 membered saturated unsubstituted or substituted heterocyclic ring comprising the nitrogen atom which is attached to the quinazoline ring and, wherein the ring A substituted heterocyclic ring has one or more substituents independently selected from alkoxy, hydroxy or hydroxyalkyl.
10. The compound according to claim 9, wherein A is pyrrolidinyl or pyrrolidinyl substituted with hydroxymethyl, methoxy or ethoxy.
11. The compound according to claim 1 selected from
4-(2-Methyl-4-pyrrolidin-1-yl-quinazolin-7-yloxymethyl)-benzonitrile;
7-(2-Chloro-pyridin-3-ylmethoxy)-2-methyl-4-pyrrolidin-1-yl-quinazoline;

7-(2-Fluoro-pyridin-3-ylmethoxy)-2-methyl-4-pyrrolidin-1-yl-quinazoline;
(S)-{1-1[7-(2-Chloro-pyridin-3-ylmethoxy)-2-methyl-quinazolin-4-yl]-pyrrolidin-2-yl}-methanol;
(S)-4-[4-(3-Ethoxy-pyrrolidin-1-yl)-2-methyl-quinazolin-7-yloxymethyl]-benzonitrile;
Isobutyl-(2-methyl-4-pyrrolidin-1-yl-quinazolin-7-yl)-amine;
(2-Methyl-4-pyrrolidin-1-yl-quinazolin-7-yl)-pyridin-3-yl-amine;
Furan-2-carboxylic acid (2-methyl-4-pyrrolidin-1-yl-quinazolin-7-yl)-amide;
(S)-[4-(3-Ethoxy-pyrrolidin-1-yl)-2-methyl-quinazolin-7-yl]-pyridin-3-yl-amine; and
(S)-[4-(3-Methoxy-pyrrolidin-1-yl)-2-methyl-quinazolin-7-yl]-pyridin-3-yl-amine.

12. A pharmaceutical composition comprising a therapeutically effective amount of a compound in accordance with claim 1 and a pharmaceutically acceptable carrier.

13. A method of treatment of obesity in a patient in need of such treatment which comprises administering to the patient a therapeutically effective amount of from about 0.1 mg to 20 mg per kg body weight per day of the compound according to claim 1.

14. A method of treatment of obesity in a patient in need of such treatment which comprises administering to the patient a therapeutically effective amount from about 0.1 mg to 20 mg per kg body weight per day of the compound according to claim 1 and a therapeutically effective amount of from 60 to 720 mg per day of orlistat.

15. The method according to claim 14 wherein the compound according to claim 1 and the orlistat are administered simultaneously, separately or sequentially.

16. The pharmaceutical composition of claim 12 further comprising a therapeutically effective amount of orlistat.

* * * * *